(12) United States Patent
Minagawa et al.

(10) Patent No.: US 9,394,391 B2
(45) Date of Patent: Jul. 19, 2016

(54) SURFACE MODIFICATION METHOD, SURFACE-MODIFIED ELASTIC BODY, GASKET FOR INJECTOR, INJECTOR, AND TIRE

(71) Applicants: SUMITOMO RUBBER INDUSTRIES, LTD., Kobe-shi, Hyogo (JP); KYUSHU UNIVERSITY, Fukuoka-shi, Fukuoka (JP)

(72) Inventors: Yasuhisa Minagawa, Kobe (JP); Yasuhiko Kondo, Kobe (JP); Tetsuo Mizoguchi, Kobe (JP); Atsushi Takahara, Fukuoka (JP); Motoyasu Kobayashi, Fukuoka (JP)

(73) Assignees: SUMITOMO RUBBER INDUSTRIES, LTD., Kobe-Shi (JP); KYUSHU UNIVERSITY, Fukuoka-Shi (JP)

( * ) Notice: Subject to any disclaimer, the term of this patent is extended or adjusted under 35 U.S.C. 154(b) by 0 days.

(21) Appl. No.: 14/730,024

(22) Filed: Jun. 3, 2015

(65) Prior Publication Data
US 2015/0266984 A1   Sep. 24, 2015

Related U.S. Application Data

(62) Division of application No. 13/976,344, filed as application No. PCT/JP2011/080589 on Dec. 26, 2011, now Pat. No. 9,074,023.

(30) Foreign Application Priority Data

Dec. 27, 2010  (JP) ................. 2010-290705
Jun. 24, 2011  (JP) ................. 2011-140754

(51) Int. Cl.
| | |
|---|---|
| C08J 3/28 | (2006.01) |
| C08F 2/46 | (2006.01) |
| C08G 61/04 | (2006.01) |
| C08F 136/18 | (2006.01) |
| C08F 2/38 | (2006.01) |
| A61M 5/315 | (2006.01) |
| C08F 8/34 | (2006.01) |
| A61M 5/31 | (2006.01) |
| B60C 1/00 | (2006.01) |
| F16J 9/26 | (2006.01) |
| F16J 9/28 | (2006.01) |
| C08F 293/00 | (2006.01) |

(52) U.S. Cl.
CPC ............ *C08F 136/18* (2013.01); *A61M 5/3129* (2013.01); *A61M 5/31511* (2013.01); *A61M 5/31513* (2013.01); *B60C 1/0016* (2013.04); *C08F 2/38* (2013.01); *C08F 8/34* (2013.01); *C08F 293/005* (2013.01); *C08J 3/28* (2013.01); *F16J 9/26* (2013.01); *F16J 9/28* (2013.01); *A61M 2005/3131* (2013.01); *C08F 2438/01* (2013.01); *C08J 2315/02* (2013.01)

(58) Field of Classification Search
CPC ........ C08F 136/18; C08F 2/38; C08F 293/05; C08F 8/34; F16J 9/28; F16J 9/26; A61M 5/31511; A61M 2005/3131; A61M 5/3129; A61M 5/31513; B60C 1/0016; C08J 36/28; C08J 2315/02
USPC .......................................... 522/127, 1; 520/1
See application file for complete search history.

(56) References Cited

U.S. PATENT DOCUMENTS

| | | | |
|---|---|---|---|
| 6,653,429 B1 | 11/2003 | Nakagawa et al. | |
| 2008/0016644 A1 | 1/2008 | Mizote et al. | |
| 2010/0035074 A1 | 2/2010 | Cohen et al. | |
| 2010/0227077 A1* | 9/2010 | Wen ................... | A61F 2/30767 427/517 |

FOREIGN PATENT DOCUMENTS

| | | |
|---|---|---|
| JP | 61-209667 A | 9/1986 |
| JP | 2002-145971 A | 5/2002 |
| JP | 2008-24091 A | 2/2008 |

(Continued)

OTHER PUBLICATIONS

Yameen et al, Tailoring of Poly(ether ether ketone) Surface Properties via Surface-Initiated Atom Transfer Radical Polymerization, Mar. 10, 2009, Langmuir, 25(11), 6214-6220.*
Yano et al, Preparation and Surface Characterization of Surface-modified Electrospun POly(methyl methacryalte) Copolymer nanofibers, Sep. 11, 2010, Chem. Lett., 39, 1110-1111.*

(Continued)

*Primary Examiner* — Ling Choi
*Assistant Examiner* — Jessica E Whiteley
(74) *Attorney, Agent, or Firm* — Birch, Stewart, Kolasch & Birch, LLP

(57) ABSTRACT

Provided are: surface modification method for imparting slid-ability to surface of elastic body such as vulcanized rubber or thermoplastic elastomer without using expensive self-lubri-cating resin; surface-modified elastic body with polymer brush formed on its surface; and gasket for injector and injec-tor formed of surface-modified elastic body. The surface modification method applies to surface of thermoplastic elas-tomer or vulcanized rubber. The surface modification method comprises the step of forming hydroxyl group on surface of to-be-modified object such as rubber so that water contact angle of the surface becomes 8 to 50 degrees smaller than original water contact angle in unmodified condition, the step of forming polymerization initiation site by subjecting the hydroxyl group to action of secondary or tertiary organic halide, and the step of growing polymer brush on the surface of to-be-modified object by subjecting monomer to radical polymerization at the polymerization initiation site acting as a point of initiation.

13 Claims, 7 Drawing Sheets

(56) References Cited

FOREIGN PATENT DOCUMENTS

| | | |
|---|---|---|
| JP | 2008-133434 A | 6/2008 |
| JP | 2009-298872 A | 12/2009 |
| JP | 2010-142573 A | 7/2010 |

OTHER PUBLICATIONS

Yanot et al., "Preparation and Surface Characterization of Surface-modified Electorspun Poly(methyl mehtacrylate) Copolymer Nanofibers" Sep. 11, 2010, Chem. Lett, vol. 39, pp. 1110-1111.

* cited by examiner (a)  (b)

SURFACE MODIFICATION METHOD, SURFACE-MODIFIED ELASTIC BODY, GASKET FOR INJECTOR, INJECTOR, AND TIRE

CROSS REFERENCE TO RELATED APPLICATIONS

This application is a Divisional of copending application Ser. No. 13/976,344, filed on Jun. 26, 2013, which was filed as PCT International Application No. PCT/JP2011/080589 on Dec. 26, 2011, which claims the benefit under 35 U.S.C. §119(a) to Patent Application No. 2011-140754, filed in Japan on Jun. 24, 2011 and Patent Application No. 2010-290705, filed in Japan on Dec. 27, 2010, all of which are hereby expressly incorporated by reference into the present application.

TECHNICAL FIELD

The present invention relates to technologies to perform property modification on the surface of vulcanized rubber or thermoplastic elastomer for good sliding ability, and also to modified vulcanized rubber or thermoplastic elastomer.

BACKGROUND ART

In constructing a component which slides sealingly, for example, a gasket formed integrally with a plunger of a syringe, or equivalently injector for providing sealing between the plunger and the syringe, with higher importance given to sealing capability, an elastic body such as rubber that is somewhat difficult to slide smoothly has been used. It has thus heretofore been customary to apply silicone oil or the like to the sliding face of such a component. However, it has come to be pointed out that silicone oil or the like can affect biotechnological drug products that have recently appeared on the market.

In order to avoid that a slidability improving agent affects biotechnological drug products, if, for example, a poor-slidability injector having a sealing portion free of a coating of silicone oil or the like is used, during administration with it, the plunger thereof cannot be pressed smoothly, with consequent occurrence of pulsation. This leads to problems such as inaccuracy in the injection amount of a medicament and patient's discomfort.

In the interest of fulfillment of such mutually contradictory requirements, namely sealing capability and slidability in rubber, there is proposed the technology of covering the surface of a rubber sealing portion with a film of PTFE which is a resin having a self-lubricating nature (Patent literature 1).

Moreover, not only such a component as described above, but the syringe inner surface of an injector, the inner surface of piping for water supply, etc. are also required to exhibit good slidability in the presence of water. For example, in a diaphragm for use in a diaphragm pump, a diaphragm valve, or the like, by imparting higher slidability to the inner surface thereof which is exposed to liquid, it is possible to decrease fluid resistance and thereby allow the diaphragm to feed water without any loss.

As other effects that can be expected, in a tire, by decreasing fluid resistance at the surface of grooves formed in tire tread, it is possible to facilitate dissipation of water or snow in wet or snowy road conditions and thereby increase the ground contact area and contact pressure of the tread, with consequent improvement in grip performance and a higher level of safety.

In a ski plate or snowboard, by enhancing the slidability of the surface thereof which is brought into contact with snow, slip improvement can be achieved. Moreover, in a road sign, by enhancing the slidability of its surface, snow can slip off smoothly, with consequent increased visibility of the sign.

In a tire, as well as in a building, by decreasing the sliding resistance and surface tension of tire sidewall surfaces, as well as those of building walls, the tire and the building become less prone to adhesion of dirt and dust and can therefore be kept clean. Moreover, in a ship, by decreasing the sliding resistance and surface tension of its outer periphery, water resistance can be reduced during ship travel on water, and also the ship becomes less prone to adhesion of extraneous matters. In a swimming suit, by making improvements to the surface slidability of threads used therefor, water resistance can be reduced.

PRIOR ART REFERENCE

Patent Literature

Patent literature 1: Japanese Unexamined Patent Publication JP-A 2010-142573

SUMMARY OF THE INVENTION

Problems to be Solved by the Invention

However, in general, a resin having a self-lubricating nature such as PTFE is expensive, wherefore the production of self-lubricating resin processed products entails cost increases, which leads to limitation to the application of such a resin. Furthermore, a resin such as PTFE is so hard that it may pose a problem with sealing capability. In addition, the technology of applying a coating of a self-lubricating resin in film or the like form, when it is utilized in applications that necessitate durability due to e.g. repeated sliding motions rather than being utilized in applications such as a disposable pre-filled syringe as disclosed in Patent literature 1, will present uncertainty in reliability.

The present invention has been devised in view of the problems as mentioned supra, and accordingly its object is to provide a surface modification method for imparting slidability to the surface of an elastic body such as vulcanized rubber or thermoplastic elastomer without using an expensive self-lubricating resin, a surface-modified elastic body with a polymer brush formed on the surface thereof, and a gasket for injector, an injector, and a tire formed of the surface-modified elastic body.

Means for Solving the Problem

In a surface modification method pursuant to the present invention, an object to be modified is a thermoplastic elastomer or a vulcanized rubber. According to the method, a hydroxyl group is formed on the surface of the object to be modified in a manner such that the water contact angle of the surface becomes 8 to 50 degrees smaller than the value of a water contact angle in an untreated, or unmodified condition. Subsequently, a polymerization initiation site is formed by subjecting the thusly formed hydroxyl group to the action of a secondary or tertiary organic halide. From the polymerization initiation site acting as a point of initiation for polymerization, a monomer is subjected to radical polymerization to grow a polymer brush on the surface of the object to be modified.

The formation of a hydroxyl group on the surface of the object to be modified is effected by subjecting the surface to any one of ultraviolet irradiation, laser light irradiation, corona discharge, plasma treatment, electron beam irradiation, and atmospheric-pressure glow discharge, or a combination of the above techniques, or effected by converting the intramolecular double bond into a hydroxyl group through hydroboration.

In another surface modification method for a thermoplastic elastomer or a vulcanized rubber which is an object to be modified, a polymerization initiation site is formed by subjecting the hydroxyl group formed on the surface of the object to be modified to the action of a secondary or tertiary organic halide. From the polymerization initiation site acting as a point of initiation for polymerization, a monomer is subjected to radical polymerization to grow a polymer brush on the surface of the object to be modified.

It is preferable that the secondary or tertiary organic halide includes an ester halide group, and acts to form a polymerization initiation site having a secondary or tertiary organic halogen group in the co-presence of trialkylamine.

A polymerization reaction to grow a polymer brush on the surface of the object to be modified is induced by the atom transfer radical polymerization (ATRP) method using a monovalent copper compound and a base as catalysts, or the AGET ATRP method using a catalyst made of a divalent copper compound and a base and a reducing agent coexisting in a system or the ARGET ATRP method using a transition metal catalyst.

A divalent copper compound is used as the transition metal catalyst.

An organic or inorganic reductant is used as the reducing agent.

It is preferable that ascorbic acid is used as the reducing agent.

It is preferable that the monomer contains conjugated diene or a vinyl group as a polymerizable group, and, in the monomer, its substituent or side chain is combined with an ionic group such as carboxylic acid or its salts, sulfonic acid or its salts, phosphoric acid or its salts, or an amine group or its salts, or a zwitterionic group such as carboxybetaine, sulfobetaine, or phosphobetaine.

As the monomer, two or more types of monomers having different chemical structures may be used, and two polymer brushes grown on the surface of the object to be modified may be cross-linked to each other.

Ion cross-linkage or cross-linkage may be effected between the two polymer brushes with a hydrophilic group having oxygen atoms.

It is preferable that the monomer is of a type which contains diene or a vinyl group and an alkyl fluoride group.

The monomer may be of one or both of 3,3,4,4,5,5,6,6,7,7,8,8,9,9,10,10,11,11,12,12,12-heneicosafluorododecyl acrylate and 3,3,4,4,5,5,6,6,7,7,8,8,9,9,10,10,10-Heptadecafluorodecyl acrylate.

It is preferable that the monomer is a compound which is expressed by the following formula (1), (2), (3), or (4).

[Chemical formula 1]

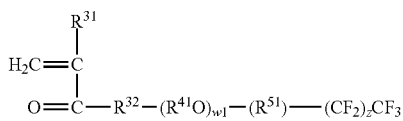

(1)

wherein $R^{31}$ represents hydrogen, a methyl group, an ethyl group, or a propyl group; $R^{32}$ represents —O—, —NH—; $R^{41}$ represents a methylene group, an ethylene group, or a propylene group; $R^{51}$ represents a ketone group ($R^{51}$ can be omitted); w1 represents an integer of 1 to 100; and z represents an integer of 1 to 6.

[Chemical formula 2]

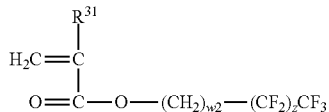

(2)

wherein $R^{31}$ represents hydrogen, a methyl group, an ethyl group, or a propyl group; w2 represents an integer of 4 to 10; and z represents an integer of 1 to 6.

[Chemical formula 3]

(3)

wherein $R^{31}$ represents hydrogen, a methyl group, an ethyl group, or a propyl group; w3 and w4 represent an integer of 1 to 6 independently; and z represents an integer of 1 to 6.

[Chemical formula 4]

(4)

wherein $R^{31}$ represents hydrogen, a methyl group, an ethyl group, or a propyl group; w3 and w4 represent an integer of 1 to 6 independently; z represents an integer of 1 to 6; and s represents an integer of 0 to 2.

According to another surface modification method, a polymerization initiation site is formed by subjecting the hydroxyl group to the action of a secondary or tertiary organic halide. Next, a transition metal complex is formed by adding the object to be modified, a radically polymerizable monomer, at least one oxidized transition metal compound, and a ligand in a liquid such as water, alcohol, or aqueous alcohol solution which has proven that it will never cause a 500% or more swell in the volume of the object to be modified. Subsequently, after substitution of oxygen in the liquid by a blow of argon or nitrogen, argon or nitrogen-substituted reduction water, alcohol, or aqueous alcohol solution is added for polymerization of the radically polymerizable monomer. In this way, a polymer brush can be formed on the surface of the object to be modified.

According to still another surface modification method, a polymer brush is grown on the surface of the object to be modified by subjecting the monomer to radical polymerization from the polymerization initiation site acting as a point of initiation for polymerization in a manner such that the coefficient of static friction of the modified surface is less than or equal to 0.5 and the coefficient of kinetic friction thereof is less than or equal to 0.25, and the coefficient of static friction of the modified surface moistened with water is less than or equal to 0.4 and the coefficient of kinetic friction thereof moistened with water is less than or equal to 0.2.

A surface-modified elastic body pursuant to the present invention is implemented by performing property modification on the surface of a thermoplastic elastomer or vulcanized rubber. In the surface-modified elastic body, a hydroxyl group is formed on the surface in a manner such that the water contact angle of the surface becomes 8 to 50 degrees smaller than the value of a water contact angle in an untreated (yet-to-be-modified) condition. The surface-modified elastic body bears a polymer brush formed by polymerizing a monomer at a polymerization initiation site, which is formed as a point of initiation for polymerization by causing a secondary or tertiary organic halide to bind to the hydroxyl group, by the atom transfer radical polymerization (ATRP) method.

It is preferable that the polymer brush is expressed by any one of the following structural formulae (5) to (7).

[Chemical formula 5]

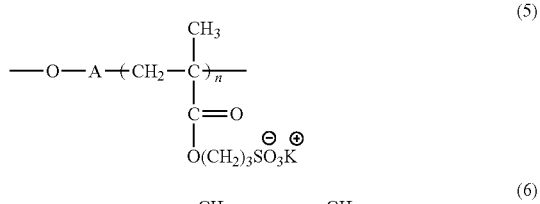

(5)

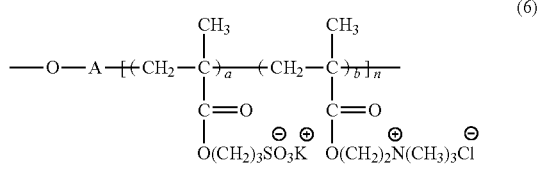

(6)

$(5 \le a/b \le 200)$

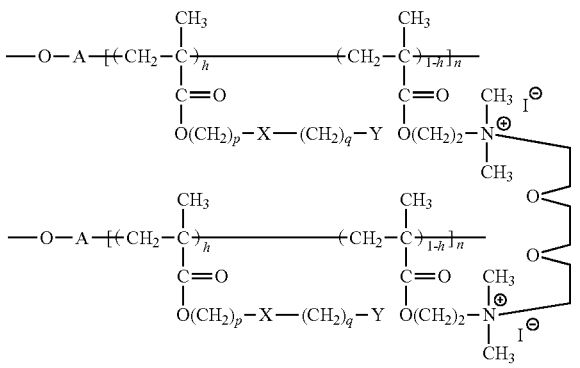

(7)

$(0.5 \le h \le 0.97), (p \ge 2, q = 2, 3, 4)$

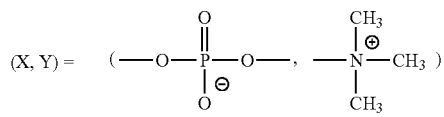

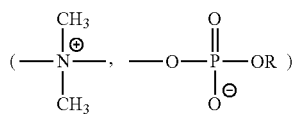

-continued wherein

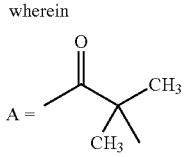   or

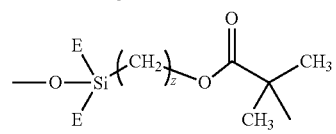

$(n \ge 100)$ $(R = CH_3, C_2H_5 \text{ or } C_3H_7)$ $(E = O-CH_3, O-C_2H_5, O-C_3H_7,$
O-vulcanized rubber or O-thermoplastic elastomer)

The polymer brush is made of two or more types of monomers having different chemical structures, and ion cross-linkage or cross-linkage is effected between the two polymer brushes formed on the surface.

Ion cross-linkage or cross-linkage may be effected between the two polymer brushes with a hydrophilic group having oxygen atoms.

The monomer may be of a type which contains diene or a vinyl group and an alkyl fluoride group.

It is preferable that the length of the polymer brush falls in the range of 10 nm or above to 50000 nm or below.

It is preferable that the coefficient of static friction of the modified surface is less than or equal to 0.5 and the coefficient of kinetic friction thereof is less than or equal to 0.25, and the coefficient of static friction of the modified surface moistened with water is less than or equal to 0.4 and the coefficient of kinetic friction thereof moistened with water is less than or equal to 0.2.

An injector pursuant to the present invention is so designed that a plunger integrally formed with a gasket made of a thermoplastic elastomer or a vulcanized rubber slides over the inner surface of a syringe. On the surface of the sliding face of the gasket, a polymer brush is formed by following a step of forming a hydroxyl group in a manner such that the water contact angle of the surface becomes 8 to 50 degrees smaller than the value of a water contact angle in an unmodified condition and a step of polymerizing a monomer from a polymerization initiation site, which is formed as a point of initiation for polymerization by causing a secondary or tertiary organic halide to bind to the hydroxyl group, by the atom transfer radical polymerization (ATRP) method, the AGET ATRP method, or the ARGET ATRP method.

In the injector, the syringe whose inner surface receives sliding motion of the plunger may be made of a thermoplastic elastomer or a vulcanized rubber. In this case, on the inner surface of the syringe, a polymer brush is formed by following a step of forming a hydroxyl group in a manner such that the water contact angle of the sliding surface becomes 8 to 50 degrees smaller than the value of a water contact angle in an unmodified condition and a step of polymerizing a monomer from a polymerization initiation site, which is formed as a point of initiation for polymerization by causing a secondary or tertiary organic halide to bind to the hydroxyl group, by the atom transfer radical polymerization (ATRP) method, the AGET ATRP method, or the ARGET ATRP method.

A tire pursuant to the present invention is designed to have a tread formed with a groove. The tire is made of a thermoplastic elastomer or a vulcanized rubber. On the inner surface of the groove, a polymer brush is formed by following a step of forming a hydroxyl group in a manner such that the water contact angle of the surface becomes 8 to 50 degrees smaller than the value of a water contact angle in an unmodified condition and a step of polymerizing a monomer from a polymerization initiation site, which is formed as a point of initiation for polymerization by causing a secondary or tertiary organic halide to bind to the hydroxyl group, by the atom transfer radical polymerization (ATRP) method, the AGET ATRP method, or the ARGET ATRP method.

Effects of the Invention

According to the present invention, it is possible to provide a surface modification method for imparting slidability to the surface of an elastic body such as vulcanized rubber or thermoplastic elastomer without using an expensive self-lubricating resin, a surface-modified elastic body with a polymer brush formed on the surface thereof, and a gasket for injector, a syringe for injector, and a tire formed of the surface-modified elastic body.

MODES FOR CARRYING OUT THE INVENTION

Figure 1:
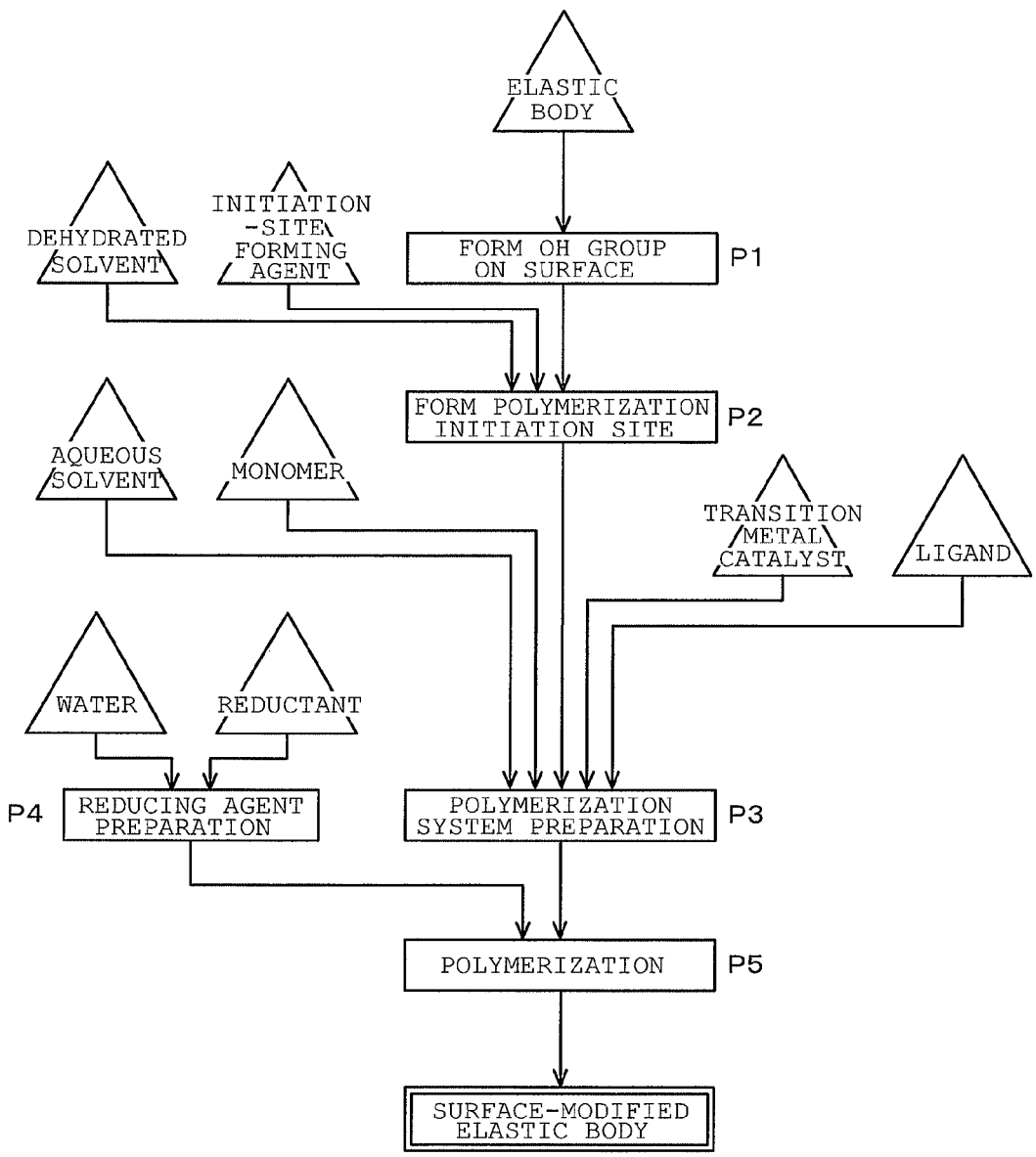
FIG. 1 is a flow diagram of a surface modification method.

FIG. 1 is a flow diagram of a surface modification method.
An object to be subjected to surface modification is a molded vulcanized rubber or a molded thermoplastic elastomer.
Examples of a target rubber include: a diene-based rubber such as styrene butadiene rubber, butadiene rubber, isoprene rubber, and natural rubber; butyl rubber; and halogenated butyl rubber.
In a case where the vulcanized rubber is butyl rubber or halogenated butyl rubber, triazine-mediated cross-linkage is advisable. This is because the amount of extract from the vulcanized rubber is relatively small. In this case, the vulcanized rubber may contain an acid-accepting agent. Hydrotalcite or magnesium carbonate is desirable for use as the acid-accepting agent.
On the other hand, where the vulcanized rubber is a diene-based rubber, sulfur vulcanization is advisable. In this case, the vulcanized rubber may contain a vulcanization accelerator, and may further contain zinc oxide.
Moreover, the vulcanized rubber may contain a filler. As the filler, the use of carbon black, silica, clay, talc, calcium carbonate, or the like is advisable.
Vulcanization is effected preferably at a temperature of higher than or equal to 150 deg. C., or more preferably at a temperature of higher than or equal to 170 deg. C., or still more preferably at a temperature of higher than or equal to 175 deg. C.

Figure 2:
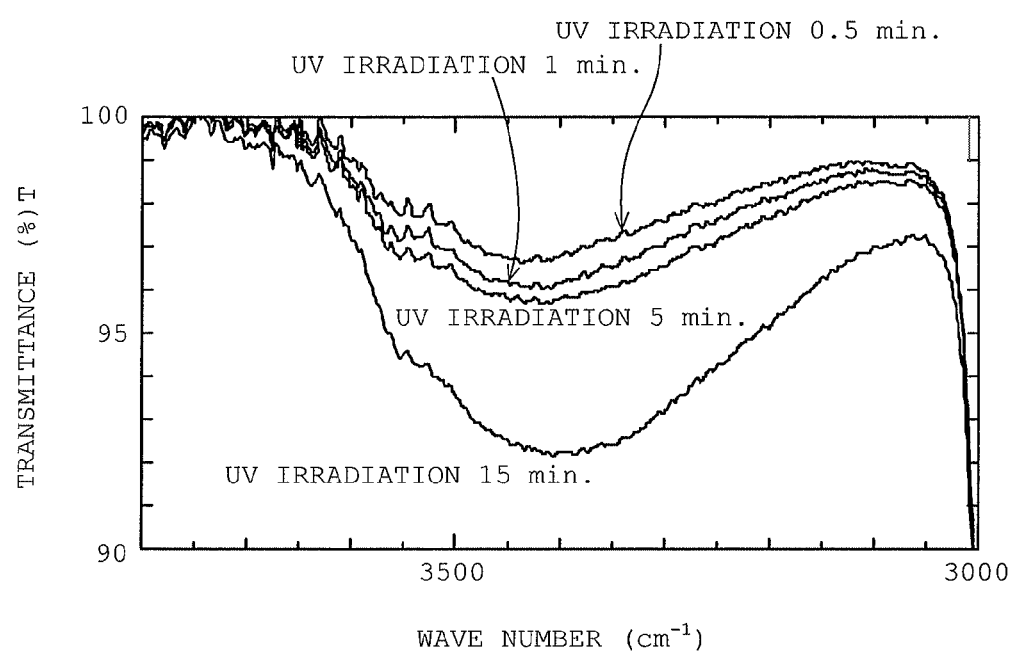
FIG. 2 is a chart indicating the relationship between ultraviolet irradiation time and transmittance of infrared spectra on the surface of an object to be modified.
Figure 3:
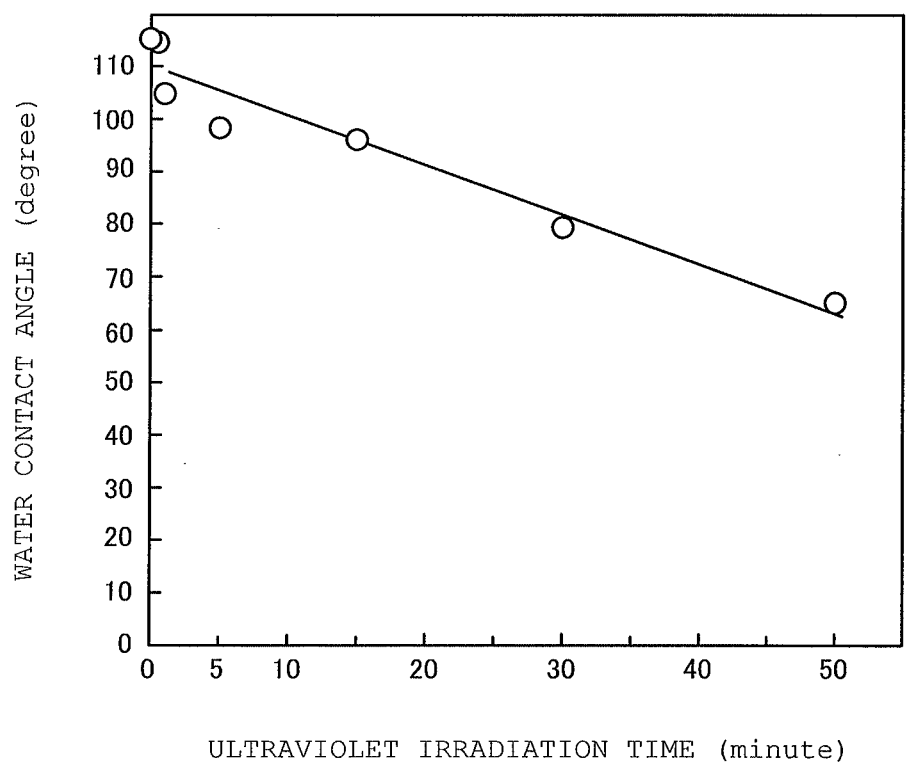
FIG. 3 is a chart indicating the relationship between ultraviolet irradiation time and water contact angle on the surface of an object to be modified.

Moreover, the vulcanized rubber may contain a silane coupling agent.
As the thermoplastic elastomer, use can be made of a polymeric compound in which a group of plastic components (hard segments) serves as a cross-linking point and soft segments (elastic components) allow the compound to exhibit elasticity at room temperature. One example of the thermoplastic elastomer is a thermoplastic elastomer (TPE) such as a styrene-butadiene-styrene copolymer. Another example thereof is an elastic polymeric compound formed by mixing a thermoplastic component and a rubber component while effecting dynamic vulcanization with a cross-linking agent, more specifically a styrene-based block copolymer or a thermoplastic vulcanizate (TPV) such as a polymer alloy formed by mixing rubber components in an olefin-based resin while dynamically vulcanizing the rubber components with a cross-linking agent.
Exemplary of the thermoplastic elastomer are nylon, polyester, urethane, polypropylene, and a dynamically vulcanized thermoplastic elastomer.
Exemplary of the dynamically vulcanized thermoplastic elastomer is a compound formed by dynamically vulcanizing halogenated butyl rubber in a thermoplastic elastomer. In such a thermoplastic elastomer, hard segments are preferably nylon, urethane, polypropylene, SIBS (styrene-isobutylene-styrene block copolymer), or the like.
Surface modification is effected by the ATRP (Atom Transfer Radical Polymerization) method based on AGET (Activators generated by electron transfer) process and ARGET (Activators regenerated by electron transfer) process for activating a catalyst repeatedly by transfer of electrons, and the procedure of surface modification involves a hydroxyl forming step P1, a polymerization initiation site forming step P2, a polymerization system preparation step P3, a reductant preparation step P4, and a polymerization step P5.
The hydroxyl forming step P1 is to impart an affinity for water, or hydrophilicity to the surface of an object to be modified. In the hydroxyl forming step P1, ultraviolet rays emitted from a low-pressure mercury lamp are applied to the object to be modified under atmospheric conditions. The low-pressure mercury lamp, which is operated at a power output on the order of 50 to 100 W, is set in a position spaced 10 to 100 mm away from a to-be-modified surface of the object to be modified, and the to-be-modified surface is irradiated with ultraviolet rays for 1 to 15 minutes.
FIG. 2 is a chart indicating the relationship between ultraviolet irradiation time and transmittance of infrared spectra on the surface of a cross-linked chlorobutyl rubber sheet, and FIG. 3 is a chart indicating the relationship between ultraviolet irradiation time and water contact angle on the surface of the cross-linked chlorobutyl rubber sheet. In FIGS. 2 and 3, the object to be irradiated with ultraviolet rays is chlorobutyl rubber formed through triazine-mediated cross-linking process.
In FIG. 2, a noticeable absorption phenomenon is found at wave numbers close to 3300 $cm^{-1}$. It will thus be understood that a hydrophilic, hydroxyl group has been formed on the surface of the cross-linked chlorobutyl rubber sheet by means of ultraviolet irradiation. It will also be seen from FIG. 2 that, the longer is the ultraviolet irradiation time, the stronger is the absorption at wave numbers close to 3300 $cm^{-1}$. It will be seen from FIG. 3 that, the longer is the ultraviolet irradiation time, the smaller is the water contact angle and thus the higher is the surface hydrophilicity. In reference to FIG. 3, water contact angle measurement has been conducted after a lapse of 20 seconds from the completion of dripping of water.
In the hydroxyl forming step P1 where a hydroxyl group is formed on the surface of the object to be modified, hydroxyl formation is not effected on all of the monomer units constituting the object to be modified, but effected only on part of them in need of modification, in other words, part of them required to exhibit slidability. The extent of hydroxyl formation on the surface of the object to be modified is controlled on the basis of ultraviolet irradiation time. For example, in the case shown in FIGS. 2 and 3, ultraviolet irradiation time corresponds to the period of time that the value of a water contact angle in an ultraviolet-irradiated condition becomes 8 to 50 degrees lower than the value of an original water contact angle in an unmodified condition. More preferably, the period of time that the former value becomes 15 to 50 degrees lower than the latter value is selected.

The following are the reasons for adjusting ultraviolet irradiation time in a manner such that the water contact angle value in the ultraviolet-irradiated condition becomes 8 to 50 degrees lower than that in the unmodified condition. That is, if the water contact angle in the ultraviolet-irradiated condition is less-than-8 degrees lower than that in the unmodified condition, the surface cannot be rendered hydroxylic properly, which leads to a failure to impart good slidability to a surface-modified product obtained through the polymerization step P5. On the other hand, if the water contact angle in the ultraviolet-irradiated condition is greater-than-50 degrees lower than that in the unmodified condition, in addition to an increase in hydroxyl groups, there arises an increase in unreactive, or weakly-reactive groups such as other types of the group defined by the rational formula of C=O. Furthermore, if the water contact angle in the ultraviolet-irradiated condition is unduly low compared to that in the unmodified condition, there arises appreciable cleavage of the main chain of a rubber molecule in itself, which leads to a failure to attain the required rubber strength for actual use. As described previously, it is particularly preferable that the water contact angle in the ultraviolet-irradiated condition is 15 to 50 degrees lower than that in the unmodified condition. This is because, in this case, since the rate of hydroxyl formation stands at a desired level, it is possible to increase the density of the polymer brush and thereby achieve further reduction in sliding resistance.

When the water contact angle in the ultraviolet-irradiated condition was less-than-8 degrees lower than that in the unmodified condition, the hydroxyl formation on the surface was not enough, and consequently it was impossible to attain good slidability even after the subsequent polymerization step P5. On the other hand, when the water contact angle in the ultraviolet-irradiated condition was greater-than-50 degrees lower than that in the unmodified condition, due to problems such as an increase in non-reactive carbonyl groups and the cleavage of the main chain of the object to be modified, the strength of the surface-modified elastic body was deteriorated.

The hydroxyl forming step P1 can be accomplished by another method. Examples of adoptable methods include: a technique to form a hydroxyl group by applying laser light to the surface of the object to be modified; a technique to form a hydroxyl group on that surface by corona discharge; a technique to form a hydroxyl group on that surface by plasma treatment; a technique to form a hydroxyl group on that surface by electron beam irradiation; a technique to form a hydroxyl group on that surface by atmospheric-pressure glow discharge; and a combination of the above techniques. In another alternative, for example, there is a method to achieve hydroxyl formation by the addition of borane (boron hydride) through hydroboration of the intramolecular double bond with subsequent oxidation of borane using hydroxyl base (NaOH, for example).

In the polymerization initiation site forming step P2, a secondary or tertiary halide (a halide containing an ester bond is desirable) is dissolved in dehydrated acetone (solvent), and the resultant solution is stirred for several hours at room temperature (ambient temperature). In this way, the secondary or tertiary halide is added to the hydroxyl group formed on the surface of the object to be modified.

The secondary or tertiary halide refers to 2-bromoisobutyryl bromide and 6'-trialkoxysilyl hexyl-2-bromoisobutyrate as well.

Triethylamine, pyridine, or the like is used as the base for the sake of trapping hydrogen halide (HBr, for example) generated by reactions.

After having been treated with the secondary or tertiary halide for a predetermined period of time, the object to be modified is taken out of the stirring equipment, and the adherent solvent is removed by vaporization.

The polymerization system preparation step P3 is to prepare a polymerization system for forming a polymer brush on the surface of the object to be modified by graft polymerization. In the polymerization system preparation step P3, a monomer to be polymerized first is dissolved in water, water-soluble alcohol, or aqueous alcohol solution. Subsequently the object to be modified bearing the halide at its surface is immersed in the water or other containing the monomer in a dissolved state. In this solution, a transition metal compound and a ligand for complexation with the transition metal compound are added for production of enough transition metal complexes. Then, an inert gas, for example, argon gas is introduced (bubbling) into the solution to remove dissolved oxygen.

As the monomer, use can be made of a compound which bears conjugated diene or a vinyl group as a polymerizable group, with its substituent or side chain combined with an ionic group such as carboxylic acid or its salts, sulfonic acid or its salts, phosphoric acid or its salts, or an amine group or its salts, or a zwitterionic group such as carboxybetaine, sulfobetaine, or phosphobetaine.

The zwitterionic monomer is expressed in general-formula form as:

$$CH_2=CRCOO(CH_2)_pX(CH_2)_qY \qquad (8)$$

wherein R represents an alkyl group having a hydrogen or carbon number of 6 or less; p represents an integer of 2 or more; q represents an integer of 2 to 4; and X and Y represent ionic functional groups having opposite electrical charges, respectively. Exemplary of X is tetraalkyl ammonium, phosphonate, or the like, whereas exemplary of Y is carboxylic acid, sulfonic acid, phosphonate, tetraalkyl ammonium, or the like.

The monomer may be of at least one substance selected from 3,3,4,4,5,5,6,6,7,7,8,8,9,9,10,10,11,11,12,12,12-heneicosafluorododecyl acrylate, 3,3,4,4,5,5,6,6,7,7,8,8,9,9,10,10,10-Heptadecafluorodecyl acrylate, and the like.

Moreover, as the monomer, use can be made of a compound which is expressed by the following formula (1), (2), (3), or (4).

[Chemical formula 1]

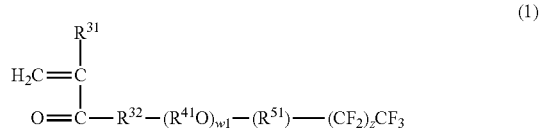

wherein $R^{31}$ represents hydrogen, a methyl group, an ethyl group, or a propyl group; $R^{32}$ represents —O—, —NH—; $R^{41}$ represents a methylene group, an ethylene group, or a propylene group; $R^{51}$ represents a ketone group ($R^{51}$ can be omitted); w1 represents an integer of 1 to 100; and z represents an integer of 1 to 6.

[Chemical formula 2]

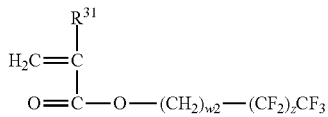
(2)

wherein $R^{31}$ represents hydrogen, a methyl group, an ethyl group, or a propyl group; w2 represents an integer of 4 to 10; and z represents an integer of 1 to 6.

[Chemical formula 3]

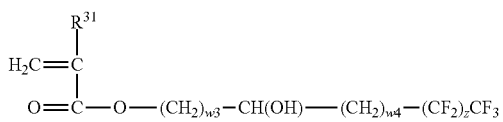
(3)

wherein $R^{31}$ represents hydrogen, a methyl group, an ethyl group, or a propyl group; w3 and w4 represent an integer of 1 to 6 independently; and z represents an integer of 1 to 6.

[Chemical formula 4]

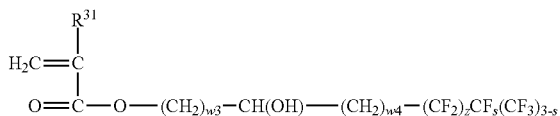
(4)

wherein $R^{31}$ represents hydrogen, a methyl group, an ethyl group, or a propyl group; w3 and w4 represent an integer of 1 to 6 independently; z represents an integer of 1 to 6; and s represents an integer of 0 to 2.

Methyl alcohol, ethyl alcohol, or isopropyl alcohol can be used as the water-soluble alcohol.

Divalent copper halide such as cupric bromide (copper (II) bromide) or cupric chloride (copper (II) chloride) can be used as the transition metal catalyst.

As the ligand which is generally used for the atom transfer radical polymerization, bipyridines such as 4,4'-dimethyl-2, 2'-bipyridine, or aliphatic amines such as N,N,N',N'',N'''-pentamethyldiethylenetriamine (PMDETA) can be used.

The reductant preparation step P4 is to prepare a reductant for the atom transfer radical polymerization. The reductant is prepared by dissolving a reducing agent, for example, ascorbic acid in water, and then introducing argon or the like to remove dissolved oxygen.

Other examples of usable reducing agents include: ascorbic acid-6-palmitate (A6P); a stannous compound; stannous oxalate; sodium sulfite; a sulfur compound in a condition of low oxidation; sodium hydrogen sulfite; inorganic salt containing metal ions; phenol; hydrazine; hydrazine hydrate; alkylamine; polyamine; pyridine and its derivatives; alkylthiol; mercaptoethanol; an easily-enolizable carbonyl compound; acetylacetonate; camphor sulfonic acid; hydroxyacetone; reduction sugar; monosaccharide; glucose and related sugar; tetrahydrofuran; dihydroanthracene; silane; 2,3 dimethylbutadiene; formamidinesulfinic acid; a silane compound; a borane compound; aldehyde; and derivatives of such compounds, for example, inorganic salts such as $Fe^{2+}$, $Al^{3+}$, $Ti^{3+}$, and $Ti^{4+}$.

The polymerization step P5 is to bind a monomer to the hydroxyl group formed on the surface of the object to be modified by the atom transfer radical polymerization. In this step, the aqueous reductant solution prepared in the reductant preparation step P4 is added to the water- or water soluble alcohol-based solution containing the dissolved monomer, in which is immersed the object to be modified, prepared in the polymerization system preparation step P3, and the resultant admixture is stirred. The polymerization step P5 is performed under conditions where reducing agents are added en masse at atmospheric pressure and at a temperature of 0 to 80 deg. C. or room temperature (ambient temperature) with or without stirring operation.

It is preferable that the time required for the polymerization step P5 falls in the range of 3 to 100 hours. If the treatment time is less than 3 hours, a polymer brush cannot be grown successfully, which makes it impossible to attain slidability. On the other hand, the treatment time in excess of 100 hours is undesirable from the economic standpoint.

Next, the effects of surface modification will be described.

First Embodiment

At a distance of 30 mm, ultraviolet rays have been applied to the surface of a vulcanized rubber obtained through cross-linkage of chlorobutyl rubber with triazine (vulcanization conditions: 180 deg. C. and 10 minutes) at the level of 700 W for 15 minutes to effect hydroxyl formation. By referring to FIG. 2, a requirement for the ultraviolet irradiation time is that a water contact angle of 80 degrees can be obtained.

Subsequently, acetone acting as a dehydrated, non-aqueous solvent and 2-bromoisobutyryl bromide acting as an initiation-site forming agent (85 mMol/L), together with the chlorobutyl rubber bearing the hydroxyl group at its surface, have been stirred in the co-presence of triethylamine (127.5 mMol/L) for 5 hours at room temperature (ambient temperature) to form the initiation site of polymerization.

Polymerization system preparation has been accomplished by dissolving 2 g of 3-sulfopropyl methacrylate potassium salt acting as a monomer in 1.0 ml of water, adding 4.0 ml of methyl alcohol in it, and immersing the chlorobutyl rubber formed with the polymerization initiation site (2 cm in length, 1 cm in width, 2 mm in thickness, and about 5.2 cm$^2$ in total surface area) in the resultant solution.

Next, 6.6 mg of cupric bromide (copper (II) bromide) (0.0030 mol, about 1,000,000 ppm) and 11.1 mg of 4,4'-dimethyl-2,2'-bipyridine were added to the solution, and bubbling has been carried out with argon for 15 minutes to expel existing oxygen from the system.

At that time, it has been assumed that there exist two polymerization initiation sites per square nanometer and the number of the polymerization initiation sites in the total area of the chlorobutyl rubber is given as 1.728×10$^{-9}$ mol.

As a liquid reductant, an aqueous solution of ascorbic acid of 0.1 M was prepared, and oxygen dissolved in it has been expelled by 3-minute bubbling with argon. 15 ml of the liquid reductant was added to the polymerization system including the chlorobutyl rubber immersed therein, and the admixture has been stirred at room temperature (ambient temperature) and at atmospheric pressure for monomer polymerization for 26 hours to grow a polymer brush.

The thusly obtained surface-modified chlorobutyl rubber bearing the polymer brush grown on its surface has been washed with water, cleaned lightly with ethylene glycol, then subjected to ultrasonic cleaning in water, and dried in a vacuum.

Second Embodiment

In implementing this embodiment, the first procedural step to the polymerization system preparation and further to the addition of the liquid reductant, and also the cleaning and other process conducted after polymerization were the same as those for the first embodiment. The only difference from the first embodiment is that the time required for polymerization involving stirring operation was set at 53.5 hours.

Third Embodiment

In implementing this embodiment, the first procedural step to the polymerization system preparation and further to the addition of the liquid reductant, and also the cleaning and other process conducted after polymerization were the same as those for the first and second embodiments. The only difference from the first and second embodiments is that the time required for polymerization involving stirring operation was set at 93.5 hours.

Fourth Embodiment

In implementing this embodiment, the first procedural step to the formation of a polymerization initiation site on the surface of the vulcanized rubber were the same as those for the first to the third embodiments.

Polymerization system preparation has been accomplished by dissolving, as a monomer, 1.92 g of 3-sulfopropyl methacrylate potassium salt and 0.08 g of 2-((metha)acryloyloxy) ethyltrimethyl ammoniumchloride (MTAC) in 1.0 ml of water, adding 4.0 ml of methyl alcohol in it, and immersing the chlorobutyl rubber formed with the polymerization initiation site in the resultant solution.

Next, 6.6 mg of cupric bromide (copper (II) bromide) and 11.1 mg of 4,4'-dimethyl-2,2'-bipyridine were added to the solution, and bubbling has been carried out with argon for 15 minutes to expel existing oxygen from the system.

As a liquid reductant, an aqueous solution of ascorbic acid of 0.1 M was prepared, and this solution has been subjected to 3-minute bubbling with argon. 0.15 ml of the aqueous ascorbic-acid solution was added to the polymerization system including the chlorobutyl rubber immersed therein, and the admixture has been stirred at room temperature (ambient temperature) for 53.5 hours for monomer polymerization to grow a polymer brush. The subsequent cleaning and other process have been conducted in the same manner as adopted in the first to third embodiments.

Fifth Embodiment

Ultraviolet rays have been applied to the surface of a vulcanized rubber obtained through cross-linkage of chlorobutyl rubber with triazine (vulcanization conditions: 180 deg. C. and 10 minutes) for 0.5 minutes to effect hydroxyl formation.

Subsequently, acetone acting as a dehydrated, non-aqueous solvent and 2-bromoisobutyryl bromide acting as an initiation-site forming agent (85 mMol/L), together with the chlorobutyl rubber bearing the hydroxyl group at its surface, have been stirred in the co-presence of triethylamine (127.5 mMol/L) for 5 hours at room temperature (ambient temperature) to form the initiation site of polymerization.

Polymerization system preparation has been accomplished by dissolving 2 g of 3-sulfopropyl methacrylate potassium salt acting as a monomer in 1.0 ml of water, adding 4.0 ml of methyl alcohol in it, and immersing the chlorobutyl rubber formed with the polymerization initiation site (2 cm in length, 1 cm in width, 2 mm in thickness, and about 5.2 $cm^2$ in total surface area) in the resultant solution.

Next, 6.6 mg of cupric bromide (copper (II) bromide) (0.0030 mol, about 1,000,000 ppm) and 11.1 mg of 4,4'-dimethyl-2,2'-bipyridine were added to the solution, and bubbling has been carried out with argon for 15 minutes to expel existing oxygen from the system.

At that time, it has been assumed that there exist two polymerization initiation sites per square nanometer and the number of the polymerization initiation sites in the total area of the chlorobutyl rubber is given as $1.728 \times 10^{-9}$ mol.

As a liquid reductant, an aqueous solution of ascorbic acid of 0.1 M was prepared, and this solution has been subjected to 3-minute bubbling with argon. 15 ml of the aqueous ascorbic-acid solution was added to the polymerization system including the chlorobutyl rubber immersed therein, and the admixture has been stirred at 40 deg. C. and at atmospheric pressure for 24 hours for monomer polymerization to grow a polymer brush.

The thusly obtained surface-modified chlorobutyl rubber bearing the polymer brush grown on its surface has been washed with water, whereafter subjected to ultrasonic cleaning in water, and dried in a vacuum.

Sixth Embodiment

In implementing this embodiment, ultraviolet rays have been applied to the surface of a vulcanized rubber for 1 minute to effect hydroxyl formation. From then on the same procedural steps as those for the fifth embodiment have been carried out to grow a polymer brush. The subsequent cleaning and other process were also the same as those for the fifth embodiment.

Seventh Embodiment

In implementing this embodiment, ultraviolet rays have been applied to the surface of a vulcanized rubber for 1 minute to effect hydroxyl formation, and the formation of a polymerization initiation site has been effected in the absence of triethylamine. From then on the same procedural steps as those for the fifth embodiment have been carried out to grow a polymer brush. The subsequent cleaning and other process were also the same as those for the fifth embodiment.

Eighth Embodiment

Ultraviolet rays have been applied to the surface of a vulcanized rubber obtained through cross-linkage of chlorobutyl rubber with triazine (vulcanization conditions: 180 deg. C. and 10 minutes) for 1 minute to effect hydroxyl formation.

Subsequently, tetrahydrofuran acting as a dehydrated, non-aqueous solvent and 2-bromoisobutyryl bromide acting as an initiation-site forming agent (425 mMol/L), together with the chlorobutyl rubber bearing the hydroxyl group at its surface, have been stirred in the co-presence of triethylamine (637.5 mMol/L) for 5 hours at room temperature (ambient temperature) to form the initiation site of polymerization.

Polymerization system preparation has been accomplished by dissolving 2 g of 3-sulfopropyl methacrylate potassium salt acting as a monomer in 1.0 ml of water, adding 4.0 ml of methyl alcohol in it, and immersing the chlorobutyl rubber formed with the polymerization initiation site (2 cm in length, 1 cm in width, 2 mm in thickness, and about 5.2 cm² in total surface area) in the resultant solution.

Next, 6.6 mg of cupric bromide (copper (II) bromide) (0.0030 mol, about 1,000,000 ppm) and 11.1 mg of 4,4'-dimethyl-2,2'-bipyridine were added to the solution, and bubbling has been carried out with argon for 15 minutes to expel existing oxygen from the system.

At that time, it has been assumed that there exist two polymerization initiation sites per square nanometer and the number of the polymerization initiation sites in the total area of the chlorobutyl rubber is given as $1.728 \times 10^{-9}$ mol.

As a liquid reductant, an aqueous solution of ascorbic acid of 0.1 M was prepared, and oxygen dissolved in it has been expelled by 3-minute bubbling with argon. 15 ml of the liquid reductant was added to the polymerization system including the chlorobutyl rubber immersed therein, and the admixture has been stirred at 40 deg. C. and at atmospheric pressure for 24 hours for monomer polymerization to grow a polymer brush.

The thusly obtained surface-modified chlorobutyl rubber bearing the polymer brush grown on its surface has been washed with water, whereafter subjected to ultrasonic cleaning in water, and dried in a vacuum.

Ninth Embodiment

In implementing this embodiment, the formation of a polymerization initiation site has been effected with use of 2-bromoisobutyryl bromide (850 mMol/L) and in the co-presence of triethylamine (1275 mMol/L). From then on the same procedural steps as those for the eighth embodiment have been carried out to grow a polymer brush. The subsequent cleaning and other process were also the same as those for the eighth embodiment.

In Table 1, there is shown the result of measurement of coefficients of static and kinetic friction on the surfaces of modified chlorobutyl rubber and unmodified chlorobutyl rubber. "Static friction coefficient after dripping of water" and "Kinetic friction coefficient after dripping of water" as presented in Table 1 each indicate a measured value of the coefficient of friction of the surface of rubber moistened with water. In the determination of coefficients of static and kinetic friction, samples have been brought into contact with borosilicate glass, and the measurement has been conducted in conformity to a testing standard ASTM D1894. The coefficients of friction have been measured under conditions where a load of 200 g is applied, the rate of tension is 600 mm/min, and the distance to be loaded is 10 cm.

Figure 4:
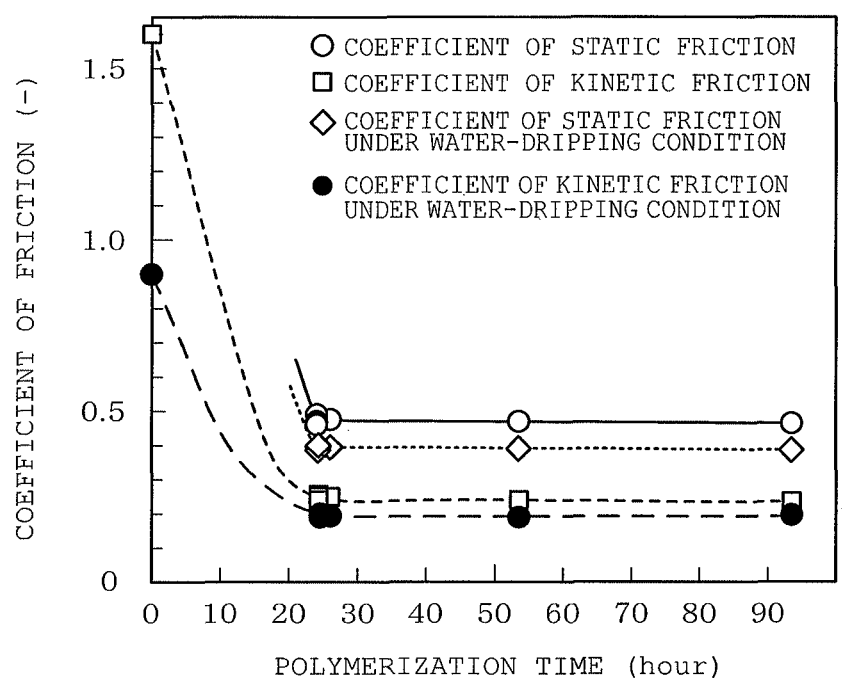
FIG. 4 is a chart indicating the relationship between polymerization time and each friction coefficient of modified surface.

FIG. 4 is a chart indicating the relationship between polymerization time and each friction coefficient in the first to ninth embodiments. In FIG. 4, each friction coefficient corresponding to zero-(minute) polymerization time is found in Comparative example 1. In reference to the "Evaluation" column of Table 1, with attention given to the values of static friction coefficients, an embodiment in which the difference between its static friction coefficient and kinetic friction coefficient is relatively small (difference of static friction coefficient after dripping of water from kinetic friction coefficient after dripping of water is less than 0.25) was rated as "Good".

It will be seen from FIG. 4 that the growth of a polymer brush on the surface of rubber helps decrease the coefficients of static and kinetic friction of the rubber and the coefficients of static and kinetic friction of the rubber whose surface has been moistened with water. Accordingly, the rubber bearing the polymer brush grown on its surface is, when used in applications that necessitate both good sealing capability and good sliding nature that are mutually contradictory functions, for example, when used in a gasket for a plunger of a syringe, capable of providing adequate sealing capability while reducing in the frictional force of the plunger acting on the syringe, and thus makes it possible to perform administration using a syringe properly with ease.

Moreover, as shown in FIG. 4, since the difference between static friction coefficient and kinetic friction coefficient is small, it is possible to make a first push of the plunger smoothly, as well as to let the plunger go into the syringe with smoothness without causing pulsation.

Next, the effect of improving water wettability produced by surface modification of a molded vulcanized rubber will be described.

A molded vulcanized rubber for use in water wettability examination was formed in the following manner.

[Raw Material]
(1) Styrene butadiene rubber (SBR) (SBR 1502 manufactured by JSR Corporation): 100 parts by weight
(2) Carbon black (DIABLACK I (trademark) manufactured by Mitsubishi Chemical Corporation): 55 parts by weight
(3) Oil (Process X140 (rubber process oil) manufactured by JX Nippon Oil & Energy Corporation): 10 parts by weight

TABLE 1

|  | Embodiment | | | | | | | | | Comparative example |
|---|---|---|---|---|---|---|---|---|---|---|
|  | 1 | 2 | 3 | 4 | 5 | 6 | 7 | 8 | 9 | 1 |
| Coefficient of static friction | 0.478 | 0.472 | 0.469 | 0.470 | 0.498 | 0.485 | 0.498 | 0.479 | 0.473 | Overloaded |
| Coefficient of kinetic friction | 0.248 | 0.245 | 0.241 | 0.242 | 0.250 | 0.249 | 0.250 | 0.246 | 0.245 | — |
| Static friction coefficient after dripping of water | 0.395 | 0.391 | 0.389 | 0.388 | 0.395 | 0.392 | 0.397 | 0.391 | 0.390 | 1.60 |
| Kinetic friction coefficient after dripping of water | 0.195 | 0.192 | 0.190 | 0.189 | 0.196 | 0.191 | 0.198 | 0.190 | 0.189 | 0.903 |
| Evaluation | Good | Good | Good | Good | Good | Good | Good | Good | Good | Poor |

(4) Zinc oxide (Zinc oxide (JIS 2) manufactured by Mitsui Mining & Smelting Co., Ltd.) 3 parts by weight
(5) Stearic acid (STEARIC ACID CAMELLIA (trademark) manufactured by NOF Corporation): 2 parts by weight
(6) Sulfur (Sulfur (200-mesh pass product) manufactured by Tsurumi Chemical Industry Co., Ltd.) 1.5 parts by weight
(7) Vulcanization accelerator (NOCCELER NS (trademark) manufactured by Ouchi Shinko Chemical Industrial Co., Ltd.) 1 part by weight The raw materials exclusive of sulfur and vulcanization accelerator have been kneaded by Banbury mixer. After the addition of sulfur and vulcanization accelerator, the kneaded product has been kneaded further by a roll. The resultant rubber has been subjected to vulcanization molding process with use of a LAT mold for 25 minutes at 170 deg. C. In the resultant annular molded vulcanized rubber 11, a groove 12 of predetermined size was formed along the outer periphery thereof by a grooving tool (electrothermal cutter).

Figure 5:
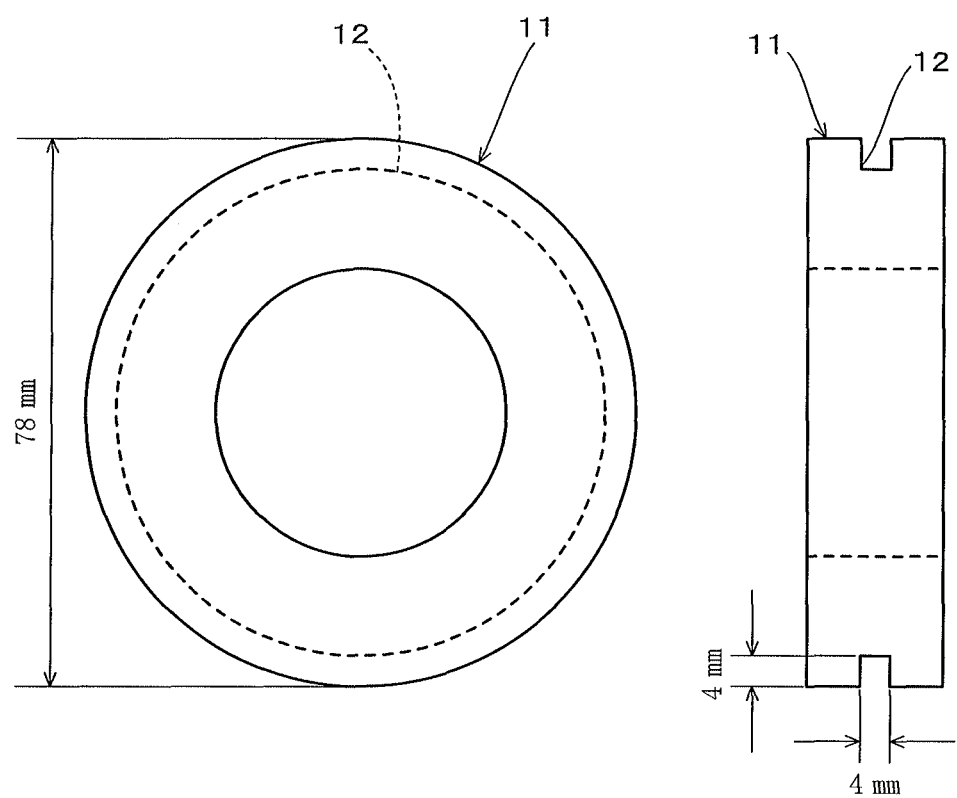
FIG. 5 is a view showing the shape of a molded vulcanized rubber which is subjected to surface modification.

FIG. 5 is a view showing the shape of the thereby prepared molded vulcanized rubber 11.

Tenth Embodiment

At a distance of 50 mm, ultraviolet rays have been applied to the groove 12 of the molded vulcanized rubber 11 at the level of 700 W for 10 minutes to effect hydroxyl formation. By referring to FIG. 2, a requirement for the ultraviolet irradiation time is that a water contact angle of 80 degrees can be obtained.

Subsequently, the molded vulcanized rubber 11, together with acetone acting as a dehydrated, non-aqueous solvent and 2-bromoisobutyryl bromide acting as an initiation-site forming agent (85 mMol/L), has been stirred in the co-presence of triethylamine (127.5 mMol/L) for 15 hours at room temperature (ambient temperature) to form the initiation site of polymerization.

Polymerization system preparation has been accomplished by dissolving 43.75 g of 3-sulfopropyl methacrylate potassium salt acting as a monomer in 70 ml of water, adding 280 ml of methyl alcohol in it, and immersing the molded vulcanized rubber 11 formed with the polymerization initiation site in the resultant solution.

Next, 115.5 mg of cupric bromide (copper (II) bromide) and 195 mg of 4,4'-dimethyl-2,2'-bipyridine were added to the solution, and bubbling has been carried out with argon for 60 minutes to expel existing oxygen from the system.

As a liquid reductant, an aqueous solution of ascorbic acid of 0.1 M was prepared, and oxygen dissolved in it has been expelled by 10-minute bubbling with argon. 5.25 ml of the liquid reductant was added to the polymerization system including the molded vulcanized rubber 11 immersed therein, and the admixture has been stirred at room temperature and at atmospheric pressure for monomer polymerization for 72 hours to grow a polymer brush.

The thusly treated molded vulcanized rubber 11 has been washed with water, whereafter subjected to ultrasonic cleaning in water, and dried in a vacuum.

Eleventh Embodiment

In implementing this embodiment, the first procedural step to the formation of a hydroxyl group at the groove 12 of the molded vulcanized rubber 11 were the same as those for the tenth embodiment.

The molded vulcanized rubber 11, together with acetone acting as a dehydrated, non-aqueous solvent and 2-bromoisobutyryl bromide acting as an initiation-site forming agent (85 mMol/L), has been stirred in the co-presence of triethylamine (127.5 mMol/L) for 5 hours at room temperature (ambient temperature) to form the initiation site of polymerization.

Polymerization system preparation has been accomplished by dissolving 21.9 g of 3-sulfopropyl methacrylate potassium salt acting as a monomer in 70 ml of water, adding 280 ml of methyl alcohol in it, and immersing the molded vulcanized rubber 11 formed with the polymerization initiation site in the resultant solution.

Next, 115.5 mg of cupric bromide (copper (II) bromide) and 195 mg of 4,4'-dimethyl-2,2'-bipyridine were added to the solution, and bubbling has been carried out with argon for 60 minutes to expel existing oxygen from the system.

As a liquid reductant, an aqueous solution of ascorbic acid of 0.1 M was prepared, and oxygen dissolved in it has been expelled by 10-minute bubbling with argon. 5.25 ml of the liquid reductant was added to the polymerization system including the molded vulcanized rubber 11 immersed therein, and the admixture has been stirred at room temperature and at atmospheric pressure for monomer polymerization for 120 hours to grow a polymer brush.

The thusly obtained surface-modified molded vulcanized rubber 11 has been washed with water, whereafter subjected to ultrasonic cleaning in water, and dried in a vacuum.

With use of the molded vulcanized rubbers 11 having the surface-modified groove implemented by way of the tenth and eleventh embodiments, respectively, and a non-surface-modified molded vulcanized rubber 11 (implemented byway of Comparative example 2) as specimens, examination has been made as to how water drainability at the groove can be changed by surface modification.

Figure 6:
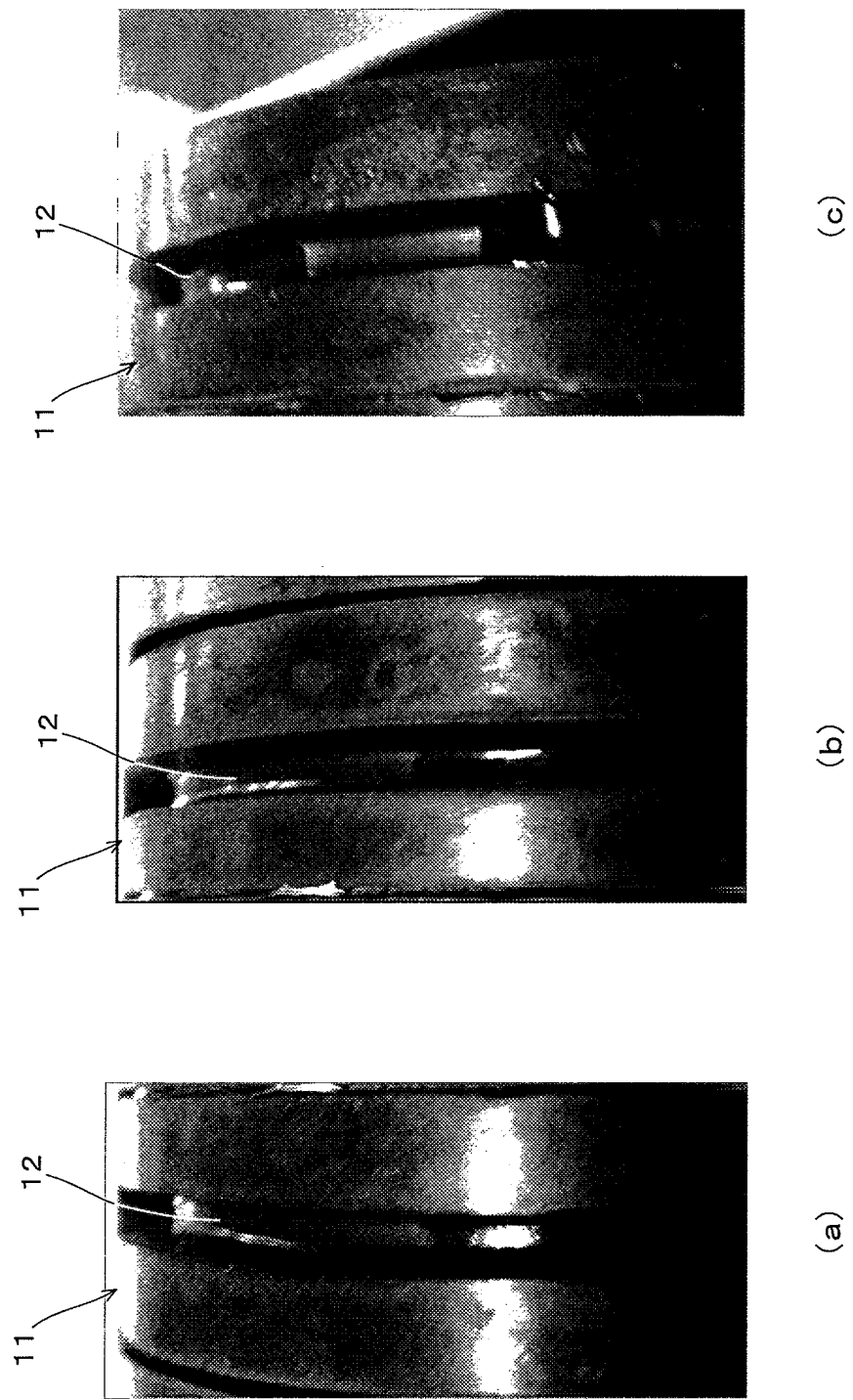
FIG. 6 is a plate showing the result of water droplet adhesion test on the groove of the molded vulcanized rubber.
Figure 7:
FIG. 7 is a plate showing the result of frost adhesion test on the groove of the molded vulcanized rubber.
Figure 7:

FIG. 6 is a plate showing the result of a water droplet adhesion test on the groove 12, and FIG. 7 is a plate showing the result of a frost adhesion test on the groove 12. In FIG. 6, (a) corresponds to the tenth embodiment, (b) corresponds to the eleventh embodiment, and (c) corresponds to Comparative example 2. In FIG. 7, (a) corresponds to the tenth embodiment and (b) corresponds to Comparative example 2.

The water droplet adhesion test has been conducted as follows. The molded vulcanized rubber 11 was supportedly placed with its center horizontal, and a droplet of water was put onto the uppermost part of the groove 12. The behavior of the water droplet has been monitored while rotating the molded vulcanized rubber 11 45 degrees in 30 seconds. According to the test result, in the molded vulcanized rubbers 11 of the tenth and eleventh embodiments, the water droplet has run down quickly upon the rotation. The rate of droplet fall as observed in the eleventh embodiment is higher than that as observed in the tenth embodiment. On the other hand, in Comparative example 2, even after 45 degree-rotation, the water droplet has remained in the groove 12. It will thus be understood that the tenth and eleventh embodiments are superior to Comparative example 2 in point of water drainability at the groove 12.

The frost adhesion test has been conducted as follows. Instead of a droplet of water used in the water droplet adhesion test, frost was put onto the groove 12, and the behavior of the frost has been monitored while rotating the molded vulcanized rubber 11 45 degrees in 30 seconds. Likewise, according to the result of the frost adhesion test, in the molded vulcanized rubber 11 of the tenth embodiment, the frost has slipped down quickly upon the rotation, whereas in Comparative example 2, even with the rotation of the molded vulcanized rubber 11, a certain amount of frost Fr has remained.

It will thus be understood that, by growing a polymer brush on the inner surface of the groove 12 as practiced in the tenth and eleventh embodiments, it is possible to facilitate dissipation of water and snow, and thereby achieve improvement in grip performance in wet and icy conditions.

Even where a thermoplastic elastomer is an object to be modified, the hydroxyl forming step P1, the polymerization initiation site forming step P2, the polymerization system preparation step P3, the reductant preparation step P4, and the polymerization step P5 can be carried out as is the case with rubber.

For example, also in the case of forming a polymer brush on the inner surface of a thermoplastic elastomer-made syringe of an injector, as described previously, administration using the injector can be carried out with ease.

Moreover, by forming a polymer brush only on a groove created at the tread of a tire for vehicles such as a passenger car, it is possible to reduce water resistance against the groove (increase water wettability) in wet conditions and thereby improve water drainability. In consequence, higher grip can be expected.

In the case of forming a polymer brush at a sidewall of a tire with use of an alkyl fluoride-based monomer, it can be expected that the tire will be resistant to adhesion of dirt.

In the case of using a polymer brush-bearing rubber or thermoplastic elastomer for a diaphragm for use in a diaphragm pump or a diaphragm valve for example, it can be expected that the delivery of water, aqueous solution, or the like can be effected with less pressure drop.

In the case of forming a polymer brush in a polymeric member (for example, polyethylene) used for a surface of a ski plate or a snowboard that slides over snow surface, or coating the sliding surface with fine powder of a rubber or a thermoplastic elastomer with a polymer brush formed at its surface, even without application of wax or the like, good sliding capability can be expected.

In a swimming suit woven of threads made of a thread material with a polymer brush formed at its surface, the resistance of water flowing on the suit surface can be reduced. It can thus be expected that the swimming suit will improve swimming race times.

In the case of covering the surface of a road sign, a signboard, or the like with a polymer brush-bearing rubber or thermoplastic elastomer, dust or snow can slip off smoothly, with consequent increased visibility of indication.

A polymer that is expressed by the following structural formulae can be adopted for a polymer brush which is formed on the surface of a vulcanized rubber or a thermoplastic elastomer by the atom transfer radical polymerization.

[Chemical formula 5]

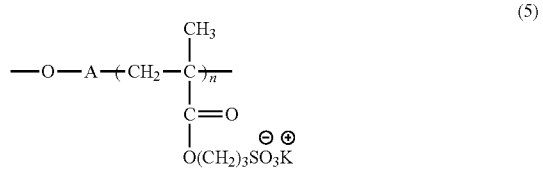

(5)

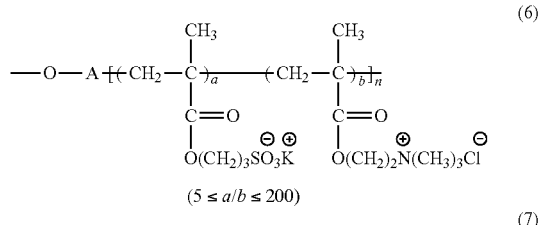

(6)

$(5 \leq a/b \leq 200)$

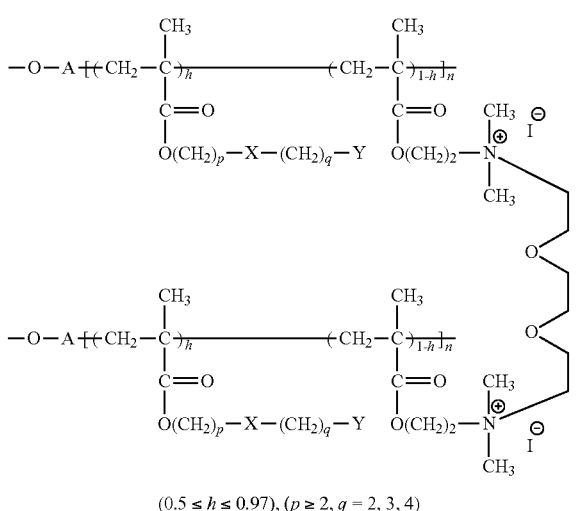

(7)

$(0.5 \leq h \leq 0.97), (p \geq 2, q = 2, 3, 4)$

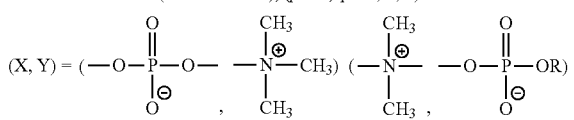

wherein

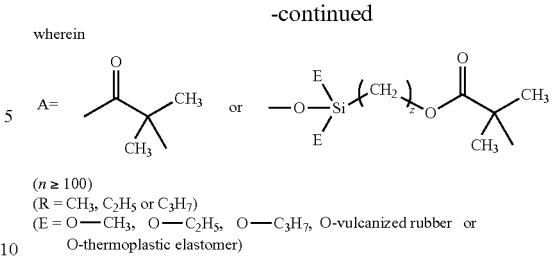

$(n \geq 100)$
$(R = CH_3, C_2H_5 \text{ or } C_3H_7)$
$(E = O-CH_3, O-C_2H_5, O-C_3H_7, \text{O-vulcanized rubber or O-thermoplastic elastomer})$ In the formula (6) and the formula (7), a, b and h, and 1-h are indicative of different monomer proportions and therefore do not represent a block copolymer. The polymer may be based either on random copolymerization or on block copolymerization. A random copolymer can be obtained by the addition of two types of monomers at one time. On the other hand, a block copolymer can be obtained by, for example, the addition of monomers in alternate order.

In the polymer brush having the structure expressed by the formula (6), the value given by a÷b falls in the range of 5 or above to 200 or below, or preferably in the range of 20 or above to 150 or below, or more preferably in the range of 30 or above to 100 or below.

The polymer brush having the structure expressed by the formula (7) was obtained through the following procedural steps. That is, in the polymerization system preparation step P3, a mixture of two types of monomers, namely MPC (2-methacryloyloxyethyl phosphorylcholine) and DMAEMA (dimethylaminoethyl methacrylate) 19:1 ratio by mole, together with cupric bromide (copper (II) bromide) and 4,4'-dimethyl-2,2'-bipyridine added in the same amounts as those set for the fourth embodiment, has been subjected to polymerization under the same conditions as those set for the fourth embodiment. Next, in the polymerization step P5, the surface-modified object with a polymer brush formed on its surface has been immersed in methyl alcohol containing dissolved 1,2-bis(2-iodoethoxy) ethane $(I(CH_2)_2O(CH_2)_2O(CH_2)_2I)$ at room temperature for 48 hours for cross-linking reaction. A cross-link part between two polymer brushes thereby formed has hydrophilic oxygen atoms.

In the formula (7), the value of h falls in the range of 0.5 or above to 0.97 or below, or preferably in the range of 0.5 or above to 0.95 or below.

The adequate range of the length of a polymer brush is from 10 nm or above to 50000 nm or below. If the length of a polymer brush is less than 10 nm, good slidability cannot be attained. On the other hand, if the length of a polymer brush is greater than 50000 nm, the slidability will no longer be enhanced, and the use of expensive monomers will entail raw-material cost increases. Furthermore, too high a polymeric level will cause a surface pattern made by surface treatment to be visible to the naked eye, which results in impairment in appearance.

INDUSTRIAL APPLICABILITY

The present invention is applicable to, for example, a sealing material required to exhibit both liquid sealing capability and surface slidability and a material required to have good water drainability at its surface as well, and can thus be utilized in equipment required to be capable of smooth yet exacting movement, such as a gasket for injector.

The invention claimed is:
1. A surface modification method for a thermoplastic elastomer or a vulcanized rubber surface comprising the steps of:
subjecting the thermoplastic elastomer or vulcanized rubber surface to ultraviolet irradiation so as to form hydroxyl groups under a condition of reducing a value of a water contact angle of said surface by 8 to 50 degrees as compared to a value of the water contact angle before irradiation on a basis of a relationship between an ultraviolet irradiation time and a decreasing degree of a value of the water contact angle after irradiation to said thermoplastic elastomer or vulcanized rubber surface;

reacting said formed hydroxyl groups with a secondary or tertiary organic halide so as to form polymerization initiation sites;

forming a transition metal complex at the polymerization initiation sites by adding a radically polymerizable monomer, at least one oxidized transition metal compound, and a ligand in a liquid selected from water, alcohol, or an aqueous alcohol solution that does not cause a 500% or more swell in the volume of the surface;

introducing argon or nitrogen gas in order to remove oxygen; and polymerizing said radically polymerizable monomer so as to form a polymer brush on said surface with addition of argon or nitrogen substituted reduction water, alcohol, or aqueous alcohol solution.

2. A surface modification method for a thermoplastic elastomer or a vulcanized rubber surface comprising the steps of:

subjecting said thermoplastic elastomer or vulcanized rubber surface to ultraviolet radiation so as to form hydroxyl groups under a condition of reducing a value of a water contact angle of the surface by 8 to 50 degrees as compared to a value of the water contact angle of the surface before irradiation on a basis of a relationship between an ultraviolet irradiation time and decreasing degree of a value of the water contact angle after irradiation to said thermoplastic elastomer or vulcanized rubber surface;

reacting a secondary or tertiary organic halide with said formed hydroxyl groups so as to form polymerization initiation sites; and subjecting said polymerization initiation sites to radical polymerization conditions together with a monomer source so as to grow a polymer brush on said surface and produce a modified surface, wherein the coefficient of static friction of the modified surface is less than or equal to 0.5, the coefficient of kinetic friction of the modified surface is less than or equal to 0.25, the coefficient of static friction of said modified surface moistened with water is less than or equal to 0.4, and the coefficient of kinetic friction of said modified surface moistened with water is less than or equal to 0.2.

3. A surface-modified elastic body, the surface-modified elastic body having a modified surface of a thermoplastic elastomer or a vulcanized rubber, wherein a polymer brush is formed by subjecting the surface to ultraviolet irradiation for a predetermined period of time to form hydroxyl groups on the surface such that a value of a water contact angle of said surface after irradiation is reduced by 8 to 50 degrees as compared to a value of the water contact angle before irradiation on a basis of a relationship between an ultraviolet irradiation time and a decreasing degree of a value of the water contact angle after irradiation to said surface of the surface-modified elastic body;

reacting the formed hydroxyl groups on the surface with a secondary or tertiary organic halide so as to form polymerization initiation sites; and subjecting the surface polymerization initiation sites to atom transfer radical polymerization (ATRP) conditions along with providing a monomer source so as to grow the polymer brush on the surface.

4. The surface-modified elastic body of claim 3, wherein said polymer brush is expressed by any one of the following structural formulae (5) to (7), wherein formula (5)

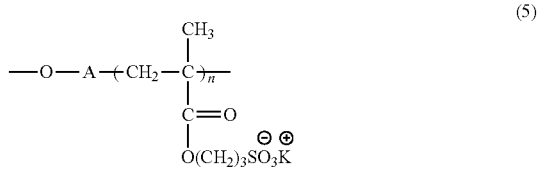

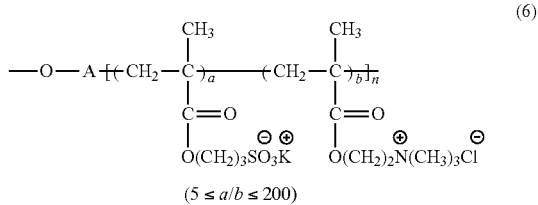

$(5 \leq a/b \leq 200)$

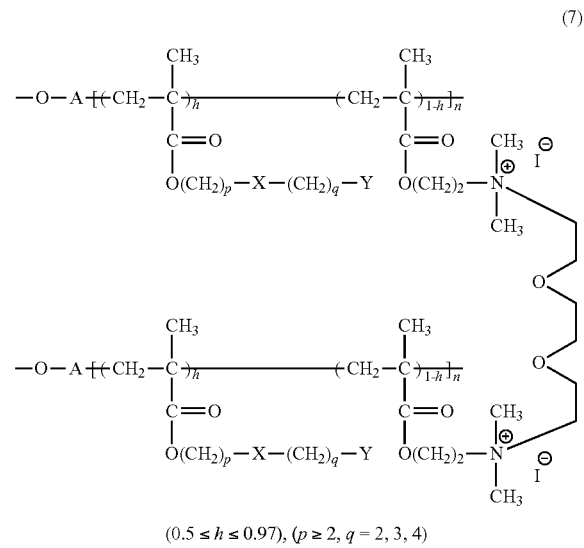

$(0.5 \leq h \leq 0.97), (p \geq 2, q = 2, 3, 4)$

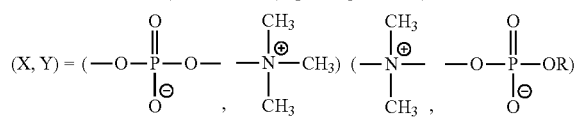

wherein

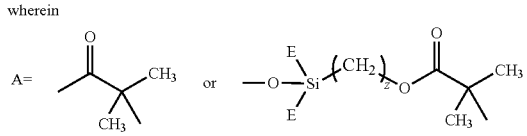

$(n \geq 100)$
$(R = CH_3, C_2H_5 \text{ or } C_3H_7)$
$(E = O-CH_3, O-C_2H_5, O-C_3H_7, O\text{-vulcanized rubber or } O\text{-thermoplastic elastomer}).$ 5. The surface-modified elastic body of claim 3, wherein said polymer brush comprises two or more types of polymers formed from two or more types of monomers having different chemical structures, and the two or more types of polymers are ion cross-linked or cross-linked.

6. The surface-modified elastic body of claim 3, wherein the ion cross-linkage or cross-linkage is formed by a hydrophilic group having oxygen atoms.

7. The surface-modified elastic body of claim 3, wherein said monomer contains a diene or a vinyl group and contains an alkyl fluoride group.

8. The surface-modified elastic body of claim 3, wherein said polymer brush has a length falling in a range of 10 nm or above to 50000 nm or below.

9. The surface-modified elastic body of claim 3, wherein the coefficient of static friction of the modified surface is less than or equal to 0.5, the coefficient of kinetic friction of the modified surface is less than or equal to 0.25, the coefficient of static friction of modified surface moistened with water is less than or equal to 0.4, and the coefficient of kinetic friction of the modified surface moistened with water is less than or equal to 0.2.

10. An injector comprising a plunger in a syringe,
wherein the plunger is integrally formed with a gasket having a thermoplastic elastomer or a vulcanized rubber surface modified with a polymer brush,
the gasket slides over an inner surface of the syringe, and
the polymer brush in the surface of the gasket is formed by subjecting a sliding surface of said gasket to said ultraviolet irradiation for a predetermined period of time to form hydroxyl groups such that a value of a water contact angle of the sliding surface of said gasket after irradiation is reduced by 8 to 50 degrees as compared to a value of the water contact angle of said surface before irradiation on a basis of a relationship between an ultraviolet irradiation time and a decreasing degree of a value of the water contact angle after irradiation to said surface of said thermoplastic elastomer or said vulcanized rubber surface;
reacting the formed hydroxyl groups on the surface with a secondary or tertiary organic halide so as to form polymerization initiation sites; and
subjecting the surface polymerization initiation sites to atom transfer radical polymerization (ATRP) conditions, activators generated by electron transfer (AGET) ATRP conditions, or activators regenerated by electron transfer (ARGET) ATRP conditions, along with providing a monomer source, so as to grow the polymer brush on the surface.

11. An injector comprising a plunger and a syringe, wherein the plunger slides over an inner surface of the syringe, said syringe is formed from a thermoplastic elastomer or a vulcanized rubber, the inner surface of said syringe is modified to have a polymer brush, and the polymer brush is formed by subjecting the inner surface of the syringe to ultraviolet irradiation for a predetermined period of time to form hydroxyl groups such that a value of a water contact angle of the inner surface of said syringe is reduced by 8 to 50 degrees as compared to a value of the water contact angle of the inner surface of said syringe before irradiation on a basis of a relationship between an ultraviolet irradiation time and a decreasing degree of a value of the water contact angle after irradiation to said surface of said thermoplastic elastomer or said vulcanized rubber surface;
reacting said formed hydroxyl groups on the surface with a secondary or tertiary organic halide so as to form polymerization initiation sites; and
subjecting the surface polymerization initiation sites to atom transfer radical polymerization (ATRP) conditions, activators generated by electron transfer (AGET) ATRP conditions, or activators regenerated by electron transfer (ARGET) ATRP conditions, along with providing a monomer source, so as to grow the polymer brush on the surface.

12. A gasket for an injector that is integrally formed with a plunger of the injector that slides over an inner surface of a syringe, wherein the gasket is formed from a thermoplastic elastomer or a vulcanized rubber, and the gasket has a surface modified with a polymer brush formed by subjecting the surface to ultraviolet irradiation for a predetermined period of time to form hydroxyl groups on the surface such that a value of a water contact angle of the surface is reduced by 8 to 50 degrees as compared to a value of the water contact angle of the surface before irradiation on a basis of a relationship between an ultraviolet irradiation time and a decreasing degree of a value of the water contact angle after irradiation to the surface of said thermoplastic elastomer or said vulcanized rubber surface;
reacting said formed hydroxyl groups on the surface with a secondary or tertiary organic halide so as to form polymerization initiation sites; and
subjecting the surface polymerization initiation sites to atom transfer radical polymerization (ATRP) conditions, activators generated by electron transfer (AGET) ATRP conditions, or activators regenerated by electron transfer (ARGET) ATRP conditions, along with providing a monomer source, so as to grow the polymer brush on the surface.

13. A tire having a tread formed with one or more grooves, wherein the tread is formed from a thermoplastic elastomer or a vulcanized rubber, the one or more grooves have an inner surface modified to have a polymer brush formed by subjecting the inner surface of said grooves to said ultraviolet irradiation for a predetermined period of time to form hydroxyl groups on the surface such that a value of a water contact angle of the surface is reduced by 8 to 50 degrees as compared to a value of the water contact angle of the surface before irradiation on a basis of a relationship between an ultraviolet irradiation time and a decreasing degree of a value of the water contact angle after irradiation to the surface of said thermoplastic elastomer or said vulcanized rubber surface;
reacting said formed hydroxyl groups on the surface with a secondary or tertiary organic halide so as to form polymerization initiation sites; and
subjecting the surface polymerization initiation sites to atom transfer radical polymerization (ATRP) conditions, activators generated by electron transfer (AGET) ATRP conditions, or activators regenerated by electron transfer (ARGET) ATRP conditions, along with providing a monomer source, so as to grow the polymer brush on the surface.

* * * * *